(12) United States Patent
Moshe et al.

(10) Patent No.: US 6,930,492 B2
(45) Date of Patent: Aug. 16, 2005

(54) USING SURFACE MICROWAVES FOR MEASURING AND DETERMINING DENSITY AND/OR MOISTURE CONTENT OF A MATERIAL

(75) Inventors: Danny S. Moshe, Kiryat Ono (IL); Alexander Greenwald, Nazareth-Illit (IL)

(73) Assignee: Malcam Ltd., Tel Aviv (IL)

(*) Notice: Subject to any disclaimer, the term of this patent is extended or adjusted under 35 U.S.C. 154(b) by 75 days.

(21) Appl. No.: 10/651,247

(22) Filed: Aug. 29, 2003

(65) Prior Publication Data
US 2005/0057263 A1 Mar. 17, 2005

Related U.S. Application Data (60) Provisional application No. 60/406,693, filed on Aug. 29, 2002.

(51) Int. Cl.$^7$ ............................................. G01R 27/04
(52) U.S. Cl. ........................ 324/637; 324/640; 324/643
(58) Field of Search ................................ 324/637–643; 34/259

(56) References Cited

U.S. PATENT DOCUMENTS 4,356,640 A * 11/1982 Jansson ........................ 34/261

2004/0124855 A1 * 7/2004 Holme et al.

* cited by examiner

Primary Examiner—Vincent Q. Nguyen
(74) Attorney, Agent, or Firm—G.E. Ehrlich (1995) Ltd.

(57) ABSTRACT

Using surface microwaves for measuring and determining density and/or moisture content of a material. Positioning material within a proximate free space region spanning immediately above surface of a surface microwave waveguide, the surface microwave waveguide includes an electrically conducting rectangular block and a dielectric rectangular insert element compactly fitting into the block. Transmitting microwaves into the first end of the surface microwave waveguide, a first portion of the transmitted microwaves propagate within the surface microwave waveguide and a second portion propagates within the proximate free space region including the material. Parameters (amplitude, phase, attenuation, and phase shift) of the propagating microwaves are perturbed by the material and are a function of density and/or moisture content of the material. Receiving the portions of propagating microwaves exiting the surface microwave waveguide, whereby the parameters of the transmitted and received microwaves are useable for determining density and/or moisture content of the material.

35 Claims, 5 Drawing Sheets

USING SURFACE MICROWAVES FOR MEASURING AND DETERMINING DENSITY AND/OR MOISTURE CONTENT OF A MATERIAL

RELATED APPLICATION

This claims the benefit of priority of U.S. provisional patent application Ser. No. 60/406,693, filed Aug. 29, 2002, entitled "Microwave Sensor For Measuring And Determining Moisture Content, Density, And Uniformity Of Materials".

FIELD AND BACKGROUND OF THE INVENTION

The present invention relates to using microwaves for measuring density and/or moisture content of materials, and more particularly, to a method, and corresponding device and system thereof, using surface microwaves for measuring and determining density and/or moisture content of a material. Microwaves are transmitted into a surface microwave waveguide having an externally exposed flat top surface immediately above which spans a proximate free space region within which the material is positioned. A portion of the transmitted microwaves propagate within and through the proximate free space region including the material, such that parameters (amplitude, phase, attenuation, and phase shift) of the propagating microwaves are perturbed by the material and are a function of density and/or moisture content of the material positioned within the proximate free space region. The propagating microwaves exiting the surface microwave waveguide are received, and the parameters (amplitude, phase, attenuation, and phase shift) of the transmitted and received microwaves are useable for determining the density and/or moisture content of the material. The present invention is generally applicable for measuring and determining density and/or moisture content of a variety of different types of dielectric materials, loose or packed, and particularly applicable to in-line measuring and determining density and/or moisture content of a relatively low density thin sheet, board, or web, of dielectric material which is continuously or intermittently moving along its longitudinal axis during the surface microwave material inspection procedure.

Manufacturing of a wide variety of consumer products, in a wide variety of industries, involves in-line processing of materials. This includes in-line processing of materials at an early, intermediate, advanced, or final stage in the overall commercial manufacturing sequence leading to a finished product. The present invention is particularly applicable to that stage of an overall commercial manufacturing sequence involving continuously or intermittently transporting or conveying a material between manufacturing processes. There exist overall commercial manufacturing sequences including a stage whereby raw or initially processed material exiting an upstream manufacturing process is formed into an intermediate material, which is then continuously or intermittently transported or conveyed to further downstream processes, eventually leading to production of bulk quantities of finished consumer product.

In going from one process to another process in a given manufacturing sequence, bulk density, moisture content, and consequently, uniformity, throughout the length of the transported or conveyed material may change, according to the particular operating or processing parameters of the processes involved. At this stage of the manufacturing sequence, bulk density, moisture content, and uniformity, are often important properties of the material which need to be determined, monitored, and controlled, prior to the material entering further downstream processes or storage. In particular, if the bulk density and/or moisture content of a given material are outside of established quality control values, use of such material is expected to lead to downstream intermediate, advanced, or final stage materials, or stored material, similarly failing their established quality control values, potentially causing undesirable rejection of material, manufacturing down time, and added cost to the finished product.

Microwave techniques, known from the prior art, are available for non-invasively determining bulk density and/or moisture content of a variety of different types of dielectric materials, during in-line processing. In these teachings, typically, a microwave radiation source beam is transmitted by a first antenna through a portion of material and the transmitted microwaves are received by a second antenna, which then produces a signal characteristic of the material and properties therein. Microwave signal parameters such as amplitude, phase, attenuation, and phase shift, are used to determine bulk density and/or moisture content of the material. Such techniques are applicable to relatively high bulk density loose or packaged materials, for example, having bulk densities of on the order of several kilograms per square meter, and provide measuring sensitivities significantly less than desirable for many current manufacturing sequences involving in-line processing of thin sheet, board, or web, configured materials. In particular, cost and quality of many current manufacturing sequences involving in-line processing of relatively low density thin sheet, board, or web, configured materials could be significantly improved if there was to exist the capability of determining and monitoring bulk density in the range of from about one kilogram to essentially zero kilogram, with corresponding measuring sensitivity of the order of one gram per square meter.

Microwave techniques for measuring density and/or moisture content of a given material are based on the direct relation of these material properties and characteristics to the dielectric properties of the material. There exist a wide variety of microwave devices which operate on the principle of transmission of microwaves through dielectric materials. These devices find wide application in laboratory measurements as well as in production lines, and they provide rapid and highly accurate measurement results.

In microwave moisture measurement, a prominent role is played by microwave devices having two antennas—one for emitting microwaves towards the dielectric material being tested, and the other for receiving the microwaves which pass through the material. The directional patterns of these antennas are such that most of the energy of the microwaves passes through the probed material. This condition determines the manner of construction and geometrical configuration of the antennas of microwave devices.

Antenna based microwave techniques find application in the measurement of density and moisture content of objects having cross sectional dimensions comparable to, or in excess of, the operable dimensions of the antennas, and whereby the path length of the microwaves within the material amounts to several wavelengths. Several examples of such antenna based microwave techniques for determining density and/or moisture content of materials are described in disclosures by the same applicant of the present invention: U.S. Pat. No. 6,107,809, entitled: "Device And Method For Non-invasively Determining Moisture Content And Density Of Loose And Packaged Tobacco"; U.S. Pat. No. 6,111,415, entitled: "Device And Method For Determining The Moisture Content Of Bulk Material"; U.S. Pat. No. 6,025,724, entitled: "Device And Method For Determining The Moisture Content Of Packaged Material"; U.S. Pat. No. 5,845,529, entitled: "Device And Method For Determining The Moisture Content Of Material"; and U.S. Pat. No. 5,621,330, entitled: "Device And Method For Determining Moisture Content Of A Bail Of Material With Multiple Layers".

In cases where the path length traveled by the microwaves within the material is less than one wavelength, sensitivity and resolving power are no longer sufficient, and to measure, for example, a thin sheet, board, or web, of dielectric material, methods and devices have been used involving multiple passage of microwaves through the probed material. Such methods and devices are disclosed in U.S. Pat. No. 4,620,146, and in U.S. Pat. No. 5,886,534. A significant limitation of these methods and devices is the occurrence of undesirable high energy losses. Lost energy inevitably finds its way into side lobes of the antenna directional pattern. Sensitivity, accuracy, and precision, of measurements are also limited by multiple diffraction and wave interference.

In the case of measuring density and/or moisture content of a relatively low density long continuous sheet, board, or web, of material, high sensitivity, accuracy, and precision, are achieved by using microwave waveguide devices. A well known method of measuring moisture content of a continuously moving thin sheet, or, woven or web, configured material, is based on using a hollow curved waveguide, for example, as disclosed in U.S. Pat. No. 3,628,135. The disclosed method suffers from the drawback of using a microwave device having relatively complex structure within which the waveguide must be configured along the direction of propagation of the microwaves while the material must be led in through a narrow slit. If this slit is widened, then energy losses inevitably increase due to sideways emission of the microwaves, and additionally, it is difficult to use such a device for measuring moisture content of loose materials.

The invention disclosed in PCT Publication No. WO 97/21992 describes a method and apparatus for measuring moisture content of materials which are based on a closed hollow waveguide with a series of slits cut into one of its walls. Part of the energy of the microwaves propagating within the waveguide is outwardly emitted through the slits. The moisture content of the material positioned close to the slit wall is measured from the coefficient of reflection of the microwaves propagating within the waveguide, which permits the determination of the moisture content of the material. The required sensitivity may be achieved for dense and moist materials which have a high coefficient of reflection, such as damp, freshly sawed, wooden planks. A thin sheet, board, or web, configured material, as well as low density loose materials, such as tobacco, are difficult to measure by this method since the coefficient of reflection from the surfaces of these materials is relatively low.

There is thus a need for, and it would be highly advantageous to have a method, and corresponding device and system thereof, using surface microwaves for measuring and determining density and/or moisture content of a material. Moreover, there is a need for such an invention which achieves high sensitivity, accuracy, and precision, of the surface microwave material inspection procedure. Additionally, there is a need for such an invention which is generally applicable for measuring and determining density and/or moisture content of a variety of different types of dielectric materials, loose or packed, and particularly applicable to in-line measuring and determining density and/or moisture content of a relatively low density thin sheet, board, or web, of dielectric material which is continuously or intermittently moving along its longitudinal axis during the surface microwave material inspection procedure. Additionally, there is a need for such an invention which is relatively inexpensive to construct and implement, and which is especially suitable for application in commercial manufacturing environments.

SUMMARY OF THE INVENTION

The present invention relates to a method, and corresponding device and system thereof, using surface microwaves for measuring and determining density and/or moisture content of a material. Microwaves are transmitted into the first end of a surface microwave waveguide having an externally exposed flat top surface immediately above which spans a proximate free space region within which the material is positioned. A first portion of the transmitted microwaves propagate within and through the surface microwave waveguide and a second portion of the transmitted microwaves propagate within and through the proximate free space region including the material, such that parameters (amplitude, phase, attenuation, and phase shift) of the propagating microwaves are perturbed by the material and are a function of density and/or moisture content of the material positioned within the proximate free space region. The propagating microwaves exiting the second end of the surface microwave waveguide are received, and the parameters of the transmitted and received microwaves are useable for determining the density and/or moisture content of the material.

The present invention provides a highly sensitive, accurate, and precise, surface microwave material inspection procedure. The present invention is generally applicable for measuring and determining density and/or moisture content of a variety of different types of dielectric materials, loose or packed, and particularly applicable to in-line measuring and determining density and/or moisture content of a relatively thin sheet, board, or web, of material which is continuously or intermittently moving along its longitudinal axis during the surface microwave material inspection procedure. The present invention is relatively inexpensive to construct and implement, and is especially suitable for application in commercial manufacturing environments.

Thus, according to the present invention, there is provided a method using surface microwaves for measuring and determining density and/or moisture content of a material, featuring the main steps of: (a) positioning the material within a proximate free space region spanning immediately above externally exposed flat top surface of a surface microwave waveguide, where the surface microwave waveguide includes: (i) an electrically conducting rectangular block including a rectangular channel which is open to free space, the open channel is defined by two parallel inner side walls of the block and a third inner bottom wall of the block orthogonally joining the side walls, the open channel extends along entire length of the block, the non-channel top surface of the block is flat and externally exposed to free space; and (ii) a dielectric rectangular insert element compactly fitting into and along the open channel in between the parallel inner side walls of the block and extending along the entire length of the block, each of first end and second end of the insert element is contiguous with corresponding first end and second end of the block, the top surface of the insert element is flat, externally exposed to free space, and contiguous with the non-channel flat top surface of the block such that the flat top surface of the insert element and the non-channel flat top surface of the block form the externally exposed flat top surface of the surface microwave waveguide; (b) transmitting microwaves into the first end of the surface microwave waveguide, such that a first portion of the transmitted microwaves propagate within and through the surface microwave waveguide and a second portion of the transmitted microwaves propagate within and through the proximate free space region including the material, such that parameters (amplitude, phase, attenuation, and phase shift) of the propagating microwaves are perturbed by the material and are a function of density and/or moisture content of the material within the proximate free space region; and (c) receiving the first portion and the second portion of the propagating microwaves exiting the second end of the surface microwave waveguide, for forming received microwaves, the parameters of the transmitted microwaves and of the received microwaves are useable for determining the density and/or moisture content of the material.

According to another aspect of the present invention, there is provided a device using surface microwaves for measuring and determining density and/or moisture content of a material, herein, also referred to as the surface microwave device, of the present invention, featuring the main components: (a) a surface microwave waveguide having an externally exposed flat top surface immediately above which spans a proximate free space region within which the material is positioned, the surface microwave waveguide is comprised of: (i) an electrically conducting rectangular block including a rectangular channel which is open to free space, the open channel is defined by two parallel inner side walls of the block and a third inner bottom wall of the block orthogonally joining the side walls, the open channel extends along entire length of the block, the non-channel top surface of the block is flat and externally exposed to free space; and (ii) a dielectric rectangular insert element compactly fitting into and along the open channel in between the parallel inner side walls of the block and extending along the entire length of the block, each of first end and second end of the insert element is contiguous with corresponding first end and second end of the block, top surface of the insert element is flat, externally exposed to free space, and contiguous with the non-channel flat top surface of the block such that the flat top surface of the insert element and the non-channel flat top surface of the block form the externally exposed flat top surface of the surface microwave waveguide; (b) a microwave transmitter adapter assembly for transmitting microwaves into the first end of the surface microwave waveguide, such that a first portion of the transmitted microwaves propagate within and through the surface microwave waveguide and a second portion of the transmitted microwaves propagate within and through the proximate free space region including the material, such that parameters (amplitude, phase, attenuation, and phase shift) of the propagating microwaves are perturbed by the material and are a function of density and/or moisture content of the material within the proximate free space region; and (c) a microwave receiver adapter assembly for receiving the first portion and the second portion of the propagating microwaves exiting the second end of the surface microwave waveguide, for forming received microwaves, the parameters of the transmitted microwaves and of the received microwaves are useable for determining the density and/or moisture content of the material.

According to another aspect of the present invention, there is provided a system using surface microwaves for measuring and determining density and/or moisture content of a material, herein, also referred to as the surface microwave system, of the present invention, featuring the main components: (a) the previously described surface microwave device; (b) a microwave transmitter unit, operatively connected to the microwave transmitter adapter assembly of the surface microwave device, for generating and transmitting microwave radiation to the microwave transmitter adapter assembly; (c) a microwave receiver unit, operatively connected to the microwave receiver adapter assembly of the surface microwave device, for receiving the received microwaves from the microwave receiver adapter assembly; and (d) a process control and data analysis unit, operatively connected to the microwave transmitter unit and to the microwave receiver unit, for controlling the generating and transmitting of the microwave radiation by the microwave transmitter unit and of the receiving of the received microwaves by the microwave receiver unit, and, for processing and analyzing data and information generated during operation of the surface microwave device.

Implementation of the method, and corresponding device and system thereof, using surface microwaves for measuring and determining density and/or moisture content of a material, of the present invention, involves performing steps and sub-steps in a manner selected from the group consisting of manually, semi-automatically, fully automatically, and a combination thereof, and involves operation of components, mechanisms, and elements, in a manner selected from the group consisting of manual, semi-automatic, fully automatic, and a combination thereof. Moreover, according to actual steps and sub-steps, components, mechanisms, and elements, used for implementing a particular embodiment of the disclosed invention, steps and sub-steps are performed by using hardware, software, or an integrated combination thereof, and, components, mechanisms, and elements, operate by using hardware, software, or an integrated combination thereof.

In particular, software used for implementing the present invention features operatively connected and functioning written or printed data, in the form of software programs, software routines, software sub-routines, software symbolic languages, software code, software instructions or protocols, or a combination thereof. Hardware used for implementing the present invention features operatively connected and functioning electronic components and elements, in the form of a computer chip, an integrated circuit, an electronic circuit, an electronic sub-circuit, a hard-wired electrical circuit, or a combination thereof, involving digital and/or analog operations. Accordingly, an integrated combination of (1) software and (2) hardware, used for implementing the present invention, features an integrated combination of (1) operatively connected and functioning written or printed data, in the form of software programs, software routines, software sub-routines, software symbolic languages, software code, software instructions or protocols, or a combination thereof, and (2) operatively connected and functioning electronic components and elements, in the form of a computer chip, an integrated circuit, an electronic circuit, an electronic sub-circuit, a hard-wired electrical circuit, or a combination thereof, involving digital and/or analog operations.

BRIEF DESCRIPTION OF THE DRAWINGS

The present invention is herein described, by way of example only, with reference to the accompanying drawings. With specific reference now to the drawings in detail, it is stressed that the particulars shown are by way of example and for purposes of illustrative description of the preferred embodiments of the present invention only, and are presented in the cause of providing what is believed to be the most useful and readily understood description of the principles and conceptual aspects of the present invention. In this regard, no attempt is made to show structural details of the present invention in more detail than is necessary for a fundamental understanding of the invention, the description taken with the drawings making apparent to those skilled in the art how the several forms of the invention may be embodied in practice. In the drawings.

DESCRIPTION OF THE PREFERRED EMBODIMENTS

The present invention relates to a method, and corresponding device and system thereof, using surface microwaves for measuring and determining density and/or moisture content of a material. Microwaves are transmitted into the first end of a surface microwave waveguide having an externally exposed flat top surface immediately above which spans a proximate free space region within which the material is positioned. A first portion of the transmitted microwaves propagate within and through the surface microwave waveguide and a second portion of the transmitted microwaves propagate within and through the proximate free space region including the material, such that parameters (amplitude, phase, attenuation, and phase shift) of the propagating microwaves are perturbed by the material and are a function of density and/or moisture content of the material positioned within the proximate free space region. The propagating microwaves exiting the second end of the surface microwave waveguide are received, and the parameters of the transmitted and received microwaves are useable for determining the density and/or moisture content of the material.

Steps, sub-steps, components, elements, operation, and implementation of a method, and corresponding device and system thereof, using surface microwaves for measuring and determining density and/or moisture content of a material, according to the present invention, are better understood with reference to the following description and accompanying drawings. Throughout the following description and accompanying drawings, same reference numbers refer to same components or same elements.

In the following description of the method, and corresponding device and system thereof, of the present invention, included are main or principal steps and sub-steps, and main or principal devices, mechanisms, components, and elements, needed for sufficiently understanding proper 'enabling' utilization and implementation of the disclosed method and device. Accordingly, description of various possible required and/or optional preliminary, intermediate, minor, steps, sub-steps, devices, mechanisms, components, and/or elements, which are readily known by one of ordinary skill in the art, and/or which are available in the prior art and technical literature relating to application of microwave radiation technology for measuring and determining density and/or moisture content of a dielectric material, and relating to principles and practice of microwave radiation transmission, propagation, and reception, are at most only briefly indicated herein.

It is to be understood that the present invention is not limited in its application to the details of the order or sequence, and number, of steps and sub-steps of operation or implementation of the method, or to the details of type, composition, construction, arrangement, order, and number, of the components and elements of the device and system, set forth in the following description and accompanying drawings. For example, the following description refers to an electrically conducting rectangular block and a dielectric rectangular insert element fitting into the rectangular block, as main components of the surface microwave waveguide, in order to illustrate implementation of the present invention. The present invention is capable of other embodiments or of being practiced or carried out in various ways. Although steps, components, and materials, similar or equivalent to those described herein can be used for practicing or testing the present invention, suitable steps, components, and materials, are described herein.

It is also to be understood that unless otherwise defined, all technical and scientific words, terms, and/or phrases, used herein have either the identical or similar meaning as commonly understood by one of ordinary skill in the art to which this invention belongs. Phraseology, terminology, and, notation, employed herein are for the purpose of description and should not be regarded as limiting. For example, the following description refers to the proximate free space region spanning immediately above the externally exposed flat top surface of the surface microwave waveguide, of the surface microwave device, in order to illustrate implementation of the present invention. Additionally, as used herein, the term 'about' refers to ±10% of the associated value.

Immediately following, there is first a listing of the main steps of the method, and of the main components of the corresponding device and system for implementing thereof, of the present invention. Thereafter, are highlighted main aspects of novelty and inventiveness, and, beneficial and advantageous features and characteristics, of the present invention. Thereafter, are illustratively described the steps and sub-steps of the method, and the components, elements, operation, and implementation, of the device and system, of the present invention, with reference to exemplary preferred embodiments of the device and system of the present invention.

The method using surface microwaves for measuring and determining density and/or moisture content of a material, of the present invention, features the main steps of: (a) positioning the material within a proximate free space region spanning immediately above externally exposed flat top surface of a surface microwave waveguide, where the surface microwave waveguide includes: (i) an electrically conducting rectangular block including a rectangular channel which is open to free space, the open channel is defined by two parallel inner side walls of the block and a third inner bottom wall of the block orthogonally joining the side walls, the open channel extends along entire length of the block, the non-channel top surface of the block is flat and externally exposed to free space; and (ii) a dielectric rectangular insert element compactly fitting into and along the open channel in between the parallel inner side walls of the block and extending along the entire length of the block, each of first end and second end of the insert element is contiguous with corresponding first end and second end of the block, the top surface of the insert element is flat, externally exposed to free space, and contiguous with the non-channel flat top surface of the block such that the flat top surface of the insert element and the non-channel flat top surface of the block form the externally exposed flat top surface of the surface microwave waveguide; (b) transmitting microwaves into the first end of the surface microwave waveguide, such that a first portion of the transmitted microwaves propagate within and through the surface microwave waveguide and a second portion of the transmitted microwaves propagate within and through the proximate free space region including the material, such that parameters (amplitude, phase, attenuation, and phase shift) of the propagating microwaves are perturbed by the material and are a function of density and/or moisture content of the material within the proximate free space region; and (c) receiving the first portion and the second portion of the propagating microwaves exiting the second end of the surface microwave waveguide, for forming received microwaves, the parameters of the transmitted microwaves and of the received microwaves are useable for determining the density and/or moisture content of the material.

The corresponding device using surface microwaves for measuring and determining density and/or moisture content of a material, herein, also referred to as the surface microwave device, of the present invention, features the main components: (a) a surface microwave waveguide having an externally exposed flat top surface immediately above which spans a proximate free space region within which the material is positioned, the surface microwave waveguide is comprised of: (i) an electrically conducting rectangular block including a rectangular channel which is open to free space, the open channel is defined by two parallel inner side walls of the block and a third inner bottom wall of the block orthogonally joining the side walls, the open channel extends along entire length of the block, the non-channel top surface of the block is flat and externally exposed to free space; and (ii) a dielectric rectangular insert element compactly fitting into and along the open channel in between the parallel inner side walls of the block and extending along the entire length of the block, each of first end and second end of the insert element is contiguous with corresponding first end and second end of the block, top surface of the insert element is flat, externally exposed to free space, and contiguous with the non-channel flat top surface of the block such that the flat top surface of the insert element and the non-channel flat top surface of the block form the externally exposed flat top surface of the surface microwave waveguide; (b) a microwave transmitter adapter assembly for transmitting microwaves into the first end of the surface microwave waveguide, such that a first portion of the transmitted microwaves propagate within and through the surface microwave waveguide and a second portion of the transmitted microwaves propagate within and through the proximate free space region including the material, such that parameters (amplitude, phase, attenuation, and phase shift) of the propagating microwaves are perturbed by the material and are a function of density and/or moisture content of the material within the proximate free space region; and (c) a microwave receiver adapter assembly for receiving the first portion and the second portion of the propagating microwaves exiting the second end of the surface microwave waveguide, for forming received microwaves, the parameters of the transmitted microwaves and of the received microwaves are useable for determining the density and/or moisture content of the material.

The corresponding system using surface microwaves for measuring and determining density and/or moisture content of a material, herein, also referred to as the surface microwave system, of the present invention, features the main components: (a) the previously described surface microwave device; (b) a microwave transmitter unit, operatively connected to the microwave transmitter adapter assembly of the surface microwave device, for generating and transmitting microwave radiation to the microwave transmitter adapter assembly; (c) a microwave receiver unit, operatively connected to the microwave receiver adapter assembly of the surface microwave device, for receiving the received microwaves from the microwave receiver adapter assembly; and (d) a process control and data analysis unit, operatively connected to the microwave transmitter unit and to the microwave receiver unit, for controlling the generating and transmitting of the microwave radiation by the microwave transmitter unit and of the receiving of the received microwaves by the microwave receiver unit, and, for processing and analyzing data and information generated during operation of the surface microwave device.

Optionally, the surface microwave system further includes an operator workstation unit, operatively connected to the process control and data analysis unit, for an operator to provide operating commands and instructions for operating the surface microwave device, and to receive data and information generated during operation of the surface microwave device.

Optionally, the operator workstation unit in the surface microwave system includes a display device for an operator to display the operating commands and instructions and to display the received data and information generated during operation of the surface microwave device.

A main aspect of novelty and inventiveness of the present invention are based on highly effectively exploiting surface microwaves for measuring and determining density and/or moisture content of a material. This is successfully accomplished, along with achieving high sensitivity, accuracy, and precision, of the surface microwave material inspection procedure, by employing a uniquely designed, constructed, and operable, surface microwave waveguide in the surface microwave device of the present invention. The surface microwave waveguide included in the surface microwave device is so designed, constructed, and operable, such that by transmitting microwaves into the first end of the surface microwave waveguide, a first portion, typically, a major portion, of the transmitted microwaves propagate within and through the surface microwave waveguide and a second portion, typically, a minor portion, of the transmitted microwaves propagate within and through the proximate free space region including the material being tested, such that parameters (amplitude, phase, attenuation, and phase shift) of the propagating microwaves are perturbed by the material and are a function of density and/or moisture content of the material within the proximate free space region. The first and second portions of the propagating microwaves exiting the second end of the surface microwave waveguide are received, for forming received microwaves. The parameters of the transmitted microwaves and of the received microwaves are useable for determining the density and/or moisture content of the material.

A more detailed aspect of novelty and inventiveness of the present invention is that the surface microwave waveguide has an externally exposed flat top surface immediately above which spans a 'working' or 'active' proximate free space region within which the material is positioned. It is especially within and through this working or active proximate free space region that a minor portion of the transmitted microwaves propagate, in a localized manner, such that parameters (amplitude, phase, attenuation, and phase shift) of the propagating microwaves are perturbed by the material and are a function of density and/or moisture content of the material within the proximate free space region. Preferably, this working or active proximate free space region spans a height immediately above the externally exposed flat top surface of the surface microwave waveguide of about the same order of magnitude as the thickness of the material being tested.

Another more detailed aspect of novelty and inventiveness of the present invention is that operation of the surface microwave device, and system thereof, are optimized by rapidly scanning different ranges of microwave frequencies of microwaves featuring pluralities of electric field modes and magnetic field modes, sweeping around a selected microwave frequency, and receiving or collecting a plurality of signal data points within a selected frequency range, for example, a range of +/−10% of the selected frequency. The collected plurality of signal data points are used for forming data vectors. The data vectors are averaged using an empirical formula featuring parameters for maximizing sensitivity via high signal-to-noise (S/N) ratios, and for minimizing interference among the different modes of the transmitted microwaves propagating within and through the proximate free space region including the material being tested. This results in achieving high sensitivity, accuracy, and precision, of the surface microwave material inspection procedure.

The method, and corresponding device and system thereof, using surface microwaves for measuring and determining density and/or moisture content of a material, of the present invention, have several beneficial and advantageous features and characteristics, which are based on, in addition to, or a consequence of, the above described aspects of novelty and inventiveness.

First, the present invention provides a highly sensitive, accurate, and precise, surface microwave material inspection procedure.

Second, the present invention is generally applicable for measuring and determining density and/or moisture content of a variety of different types of dielectric materials, loose or packed, and particularly applicable to in-line measuring and determining density and/or moisture content of a relatively thin sheet, board, or web, of material which is continuously or intermittently moving along its longitudinal axis during the surface microwave material inspection procedure.

Third, the present invention is relatively inexpensive to construct and implement, and is especially suitable for application in commercial manufacturing environments.

Based upon the above described aspects of novelty and inventiveness, and, beneficial and advantageous features and characteristics, the present invention successfully addresses and overcomes limitations, and widens the scope, of prior art teachings of using microwave radiation for measuring and determining density and/or moisture content of a dielectric material.

The surface microwave waveguide is constructed from a material having high electrical conductivity, in a modular form or configuration having a channel and having an insert made of a dielectric material. Part of the energy of the electromagnetic field propagating along the surface microwave waveguide is localized in the immediate vicinity above the external surface of the dielectric insert, corresponding to the working or active surface of the surface microwave waveguide. The strength of the electromagnetic field diminishes exponentially with the distance extending away from the working surface of the surface microwave waveguide. The height of the layer above the working surface within which a significant part of the electromagnetic field is localized depends on the wavelength, in vacuum, and on the relative permittivity of the dielectric insert. The relation between these operating parameters is chosen so as to make the layer height and the thickness of the material under test about equal. Under this operating condition, measurable parameters of attenuation and phase shift of the surface microwave waveguide, largely depend on the density and/or the moisture content of the material under test, which is positioned in immediate proximity to the working surface of the surface microwave waveguide of the microwave device of the present invention.

In order to excite the electromagnetic field within the surface microwave waveguide, the surface microwave device of the present invention is provided with microwave input and output adapters, guiding electromagnetic energy into and out of, respectively, the surface microwave device, for enabling the surface microwave waveguide to be connected to a microwave oscillator on one side and to a microwave receiver on the other side. Each adapter is a coaxial waveguide structure having a graded junction for providing efficient coupling to the surface microwave waveguide. The specific geometrical configuration or form of the graded junction is variable, thereby providing variable specific geometrical configuration or form of the surface microwave device.

For example, use of a graded waveguide junction operably connected to a dielectric prism preferably provides a working surface of the surface microwave waveguide in the form of a strip. The entire surface microwave device then lies in the half-space bounded by the plane which passes through its working surface. This construction of the surface microwave device enables its application in a variety of production conditions, such as in-line with a conveyor belt transporting the material under test. This construction makes it possible to analyze the density and/or moisture content of continuous sheets of long length material, such as paper, veneer, plywood, chipboard, or fiber board, significantly exceeding the size of the surface microwave device.

In Step (a) of the method using surface microwaves for measuring and determining density and/or moisture content of a material, of the present invention, there is positioning the material within a proximate free space region spanning immediately above externally exposed flat top surface of a surface microwave waveguide.

Figure 1:
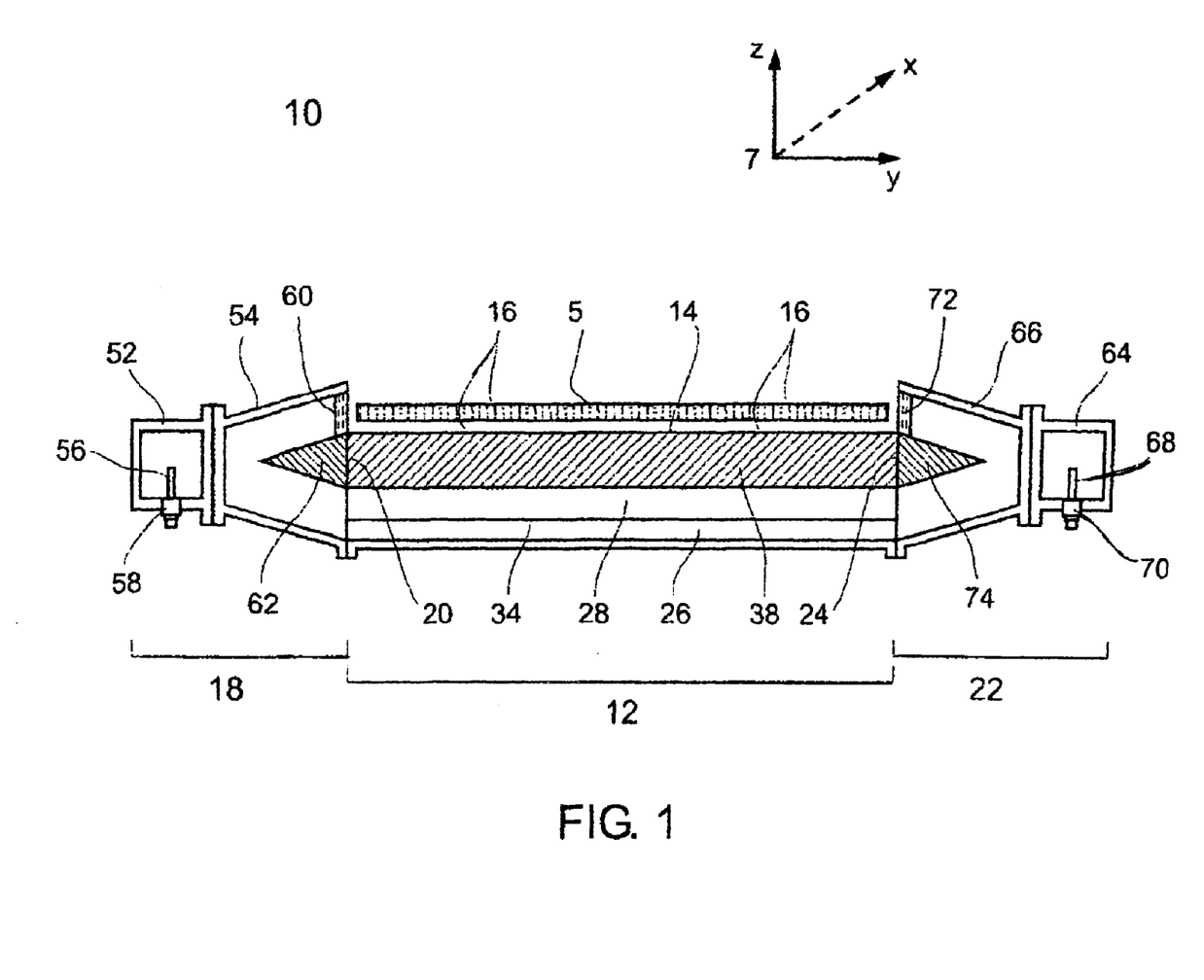
FIG. 1 is a schematic diagram illustrating a cross sectional view of an exemplary preferred embodiment of the surface microwave device, showing a material being tested, in accordance with the present invention.

Referring now to the drawings, FIG. 1 is a schematic diagram illustrating a cross sectional view of an exemplary preferred embodiment of the surface microwave device of the present invention, showing a material being tested. In FIG. 1, the surface microwave device, herein, referred to as surface microwave device 10, of the present invention, features the following primary components: (a) a surface microwave waveguide 12 having an externally exposed flat top surface 14 immediately above which spans a proximate free space region 16 within which the material 5 is positioned; (b) a microwave transmitter adapter assembly 18 for transmitting microwaves into the first end 20 of surface microwave waveguide 12, such that a first portion of the transmitted microwaves propagate within and through surface microwave waveguide 12 and a second portion of the transmitted microwaves propagate within and through proximate free space region 16 including the material 5, such that parameters (amplitude, phase, attenuation, and phase shift) of the propagating microwaves are perturbed by the material 5 and are a function of density and/or moisture content of the material 5 within proximate free space region 16; and (c) a microwave receiver adapter assembly 22 for receiving the first portion and the second portion of the propagating microwaves exiting the second end 24 of surface microwave waveguide 12, for forming received microwaves. The parameters (amplitude, phase, attenuation, and phase shift) of the transmitted microwaves and of the received microwaves are useable for determining the density and/or moisture content of the material.

Figure 2:
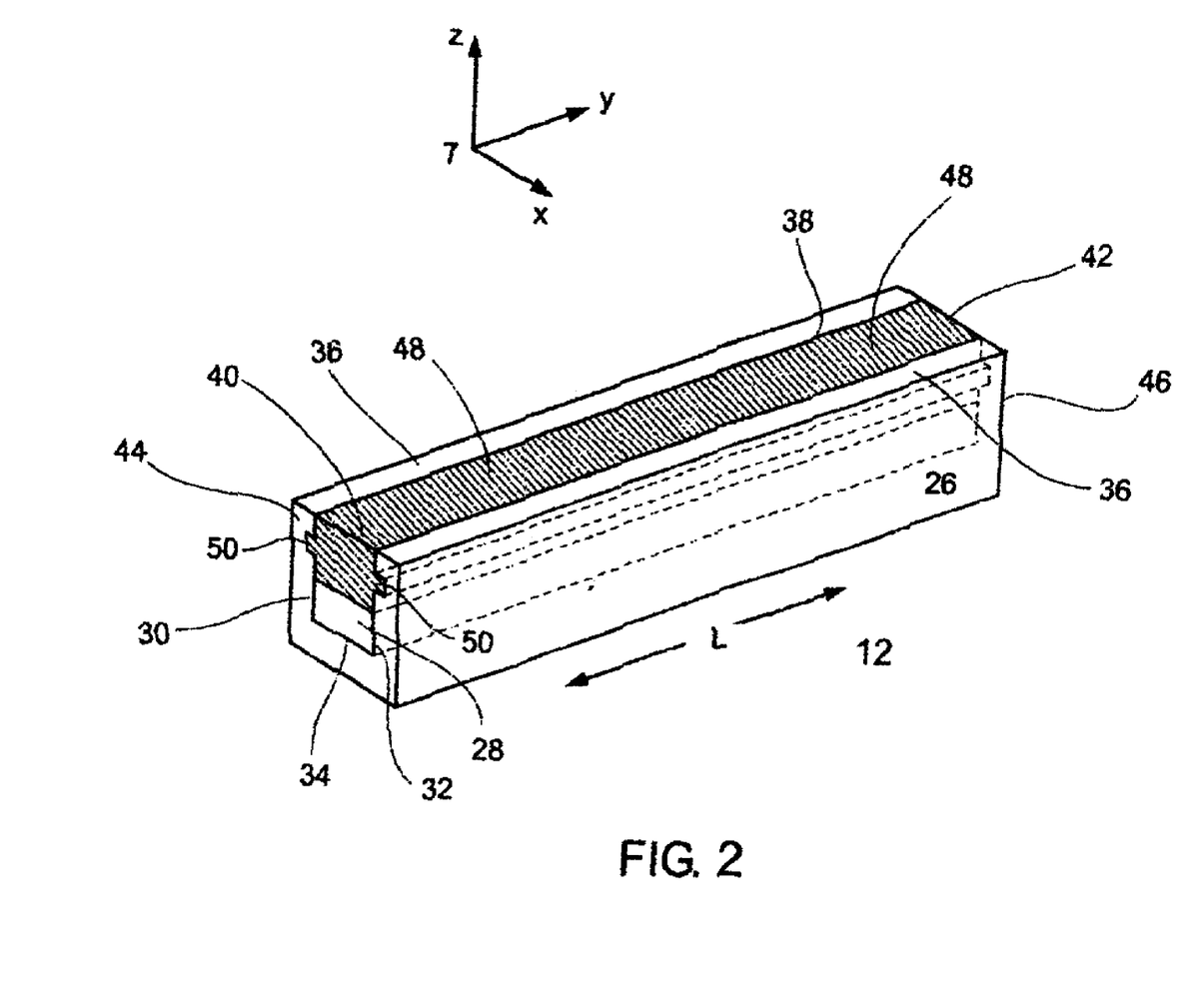
FIG. 2 is a schematic diagram illustrating a perspective view of an exemplary preferred embodiment of the surface microwave waveguide, included as part of the surface microwave device of FIG. 1, in accordance with the present invention.

Reference is now also made to FIG. 2, a schematic diagram illustrating a perspective view of an exemplary preferred embodiment of the surface microwave waveguide, surface microwave waveguide 12, included as part of the surface microwave device, surface microwave device 10, of FIG. 1, of the present invention.

Surface microwave waveguide 12 includes: (i) an electrically conducting rectangular block 26 including an open rectangular channel 28 which is open to free space. Open channel 28 is defined by two parallel inner side walls 30 and 32 of block 26 and a third inner bottom wall 34 of block 26 orthogonally joining side walls 30 and 32. Open channel extends along the entire length L of block 26. The non-channel top surface 36 of block 26 is flat and externally exposed to free space.

Surface microwave waveguide 12 additionally includes: (ii) a dielectric rectangular insert element 38 compactly fitting into and along open channel 28 in between the parallel inner side walls 30 and 32 of block 26 and extending along the entire length L (for example, with reference to reference XYZ-coordinate system 7, along the y-direction) of block 26. Each of the first end 40 and the second end 42 of insert element 38 is contiguous with the corresponding first end 44 and the second end 46 of block 26. Each of first end 44 and second end 46 of block 26, as illustrated in FIG. 2, are coincident with first end 20 and second end 24, as illustrated in FIG. 1, of surface microwave waveguide 12. The top surface 48 of insert element 38 is flat, externally exposed to free space, and contiguous with non-channel flat top surface 36 of block 26 such that flat top surface 48 of insert element 26 and non-channel flat top surface 36 of block 26 form the externally exposed flat top surface (14 as shown in FIG. 1; (48+36) as shown in FIG. 2) of surface microwave waveguide 12.

As shown in FIG. 2, the outer middle portion of dielectric rectangular insert element 38 is preferably configured in the form of a lengthwise protruding ridge 50, extending along the entire length of dielectric rectangular insert element 38, for enabling the compact fitting of dielectric rectangular insert element 38 into and along open channel 28 in between the parallel inner side walls 30 and 32 of block 26 of surface microwave waveguide 12.

Accordingly, in Step (a), there is positioning the material 5 within proximate free space region 16 spanning immediately above externally exposed flat top surface (14 as shown in FIG. 1; (48+36) as shown in FIG. 2) of surface microwave waveguide 12. The material 5 is positioned within proximate free space region 16, either contacting, or not contacting, externally exposed flat top surface (14 as shown in FIG. 1; (48+36) as shown in FIG. 2) of surface microwave waveguide 12.

The present invention is generally applicable for measuring and determining density and/or moisture content of a variety of different types of dielectric materials, loose or packed, and particularly applicable to in-line measuring and determining density and/or moisture content of a relatively thin sheet, board, or web, of material which is continuously or intermittently moving along its longitudinal axis during the surface microwave material inspection procedure. Accordingly, in general, material 5 is any type of dielectric material, loose or packed, and in particular, material 5 is a relatively thin sheet, board, or web, of material which is continuously or intermittently moving along its longitudinal axis (for example, in FIG. 1, with reference to reference XYZ-coordinate system 7, along the x-direction in the plane of the page) during the surface microwave material inspection procedure.

In Step (b), there is transmitting microwaves into first end of the surface microwave waveguide, such that a first portion of the transmitted microwaves propagate within and through the surface microwave waveguide and a second portion of the transmitted microwaves propagate within and through the proximate free space region including the material, such that parameters (amplitude, phase, attenuation, and phase shift) of the propagating microwaves are perturbed by the material and are a function of density and/or moisture content of the material within the proximate free space region.

Referring again to FIG. 1, microwave transmitter adapter assembly 18, operable for transmitting microwaves into first end 20 of surface microwave waveguide 12, includes: (1) a coaxial waveguide coupling 52, (2) a graded waveguide transition section 54, (3) a microwave input coupling pin 56, (4) a coaxial connector 58, (5) a dielectric plate 60, and (6) a dielectric matching wedge 62.

Figure 3:
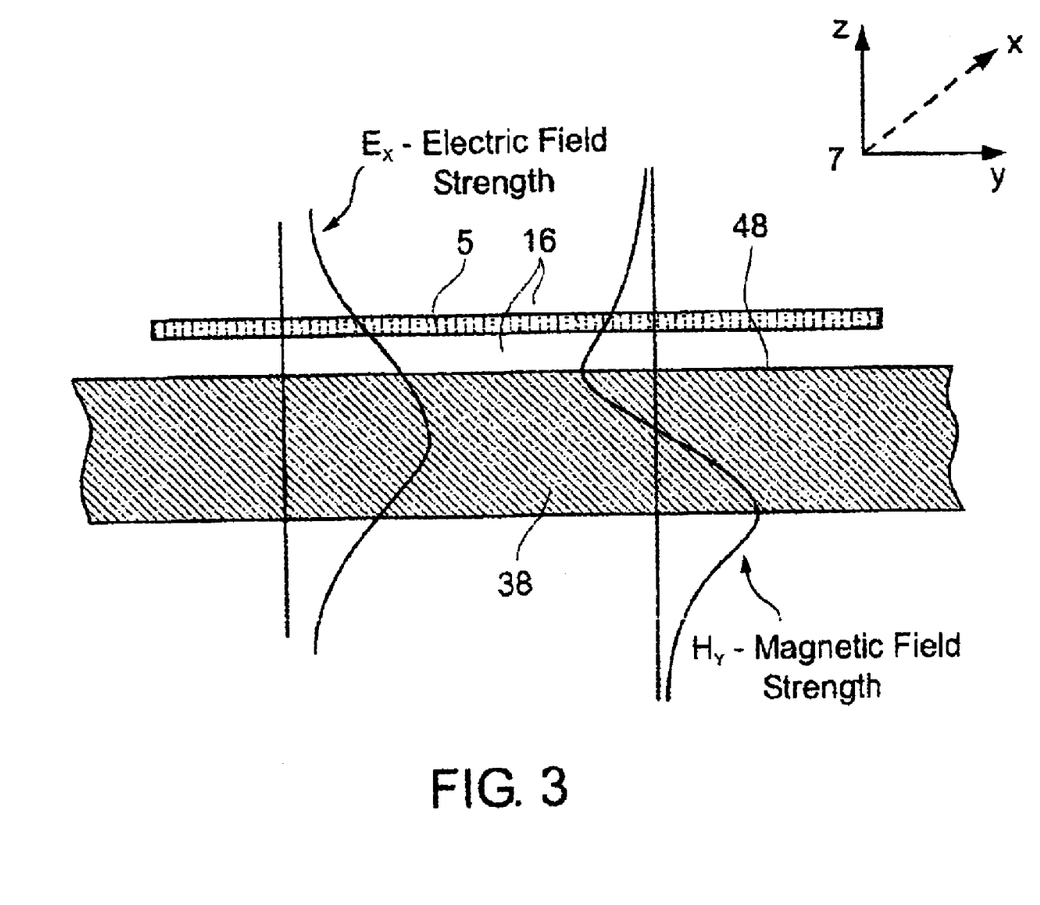
FIG. 3 is a schematic diagram illustrating exemplary gradients of the electric field strength, $E_x$, and of the magnetic field strength, $H_y$, of the microwave type of transverse electromagnetic (TE) waves propagating within and through a cross section of the dielectric rectangular insert element of the surface microwave waveguide, and propagating within and through a cross section of the proximate free space region spanning immediately above the externally exposed flat top surface of the dielectric rectangular insert element and including the material being inspected, in accordance with the present invention.

Reference is now also made to FIG. 3, a schematic diagram illustrating exemplary gradients of the electric field strength, $E_x$, and of the magnetic field strength, $H_y$, of the microwave type of transverse electromagnetic (TE) waves propagating within and through a cross section of dielectric rectangular insert element 38 of surface microwave waveguide 12 (FIGS. 1 and 2), and propagating within and through a cross section of proximate free space region 16 spanning immediately above externally exposed flat top surface 48 of dielectric rectangular insert element 38 and including the material 5 being inspected. For reference, reference XYZ-coordinate system 7 is also shown in FIG. 3.

The principle of operation of the surface microwave waveguide, surface microwave waveguide 12, of the present invention, is based on the phenomenon of microwave type of electromagnetic waves propagating in a dielectric material, that is, dielectric rectangular insert element 38, having a relative permittivity ($\epsilon$) higher than the relative permittivity of the surrounding medium. The particular construction and configuration of surface microwave waveguide 12, as illustratively described herein, enables transmission, propagation, and reception, of surface microwaves, for example, components of which are shown in FIG. 3.

The majority of the microwaves propagate within dielectric rectangular insert element 38, but under certain conditions, a considerable part of these microwaves also propagate in the proximate free space region 16 spanning immediately above externally exposed flat top surface (14 as shown in FIG. 1; (48+36) as shown in FIG. 2) of surface microwave waveguide 12, in general, and spanning immediately above externally exposed flat top surface 48 of dielectric rectangular insert element 38, in particular.

With increasing distance away from working or active proximate free space region 16, within which the material 5 is positioned, spanning immediately above externally exposed flat top surface 48 of dielectric rectangular insert element 38, of surface microwave waveguide 12, amplitudes or strengths of the electric field and the magnetic field of the propagating microwaves exponentially diminish or become attenuated. In particular, dependence of amplitudes or field strengths, $E_x$, $E_z$, and $H_y$, on the z-direction coordinate is expressed by the following equation, herein, referred to as Formula 1, as described in "Electromagnetic Waves", Someda, C. G., Chapman & Hall, 1998, p. 374–379.

$$E_x, E_z, H_y \sim \exp(-\frac{2\pi * f * z}{c} \sqrt{\left(\frac{c}{v}\right)^2 - 1}) \quad \text{Formula 1}$$

In Formula 1, $f$ is the frequency of the microwaves, $v$ is the speed of the microwaves, $c$ is the speed of light, and $z$, is the distance or height, along the z-axis, of proximate free space region 16, within which the material 5 is positioned, spanning immediately above externally exposed flat top surface 48 of dielectric rectangular insert element 38, within and through which the microwaves propagate in a localized manner.

It is seen from the relationship expressed by Formula 1, that the closer the magnitude of the microwave speed, $v$, is to the speed of light, $c$, the larger is the propagation, travel, or deflection, of the electromagnetic field in working or active proximate free space region 16, spanning immediately above externally exposed flat top surface 48 of dielectric rectangular insert element 38. It follows that by changing the speed of the propagating microwaves, it is possible to change the distance the electromagnetic field propagates, travels, or is deflected, within and through proximate free space region 16, immediately above externally exposed flat top surface 48 of dielectric rectangular insert element 38.

As an exemplary case, there is denoting h as the distance within proximate free space region 16 and immediately above externally exposed flat top surface 48 of dielectric rectangular insert element 38, up to that value of the y-direction coordinate at which the electromagnetic field strength diminishes by a factor of e, or by about 2.7. It then follows from Formula 1 that the magnitude of h depends on the microwave speed, $v$, according to the following equation, herein, referred to as Formula 2, where $\lambda$ is the free space wavelength of the microwaves:

$$h = \frac{\lambda}{2\pi * \sqrt{\left(\frac{c}{v}\right)^2 - 1}} \quad \text{Formula 2}$$

It may be shown that the ratio of the microwave speed, $v$, and the speed of light, $c$, is approximately expressed for the fundamental TE mode by the following equation, herein, referred to as Formula 3, where $\epsilon$ is the relative permittivity of dielectric rectangular insert element 38:

$$\frac{c}{v} = \sqrt{\varepsilon} \quad \text{Formula 3}$$

A dielectric material for serving as dielectric rectangular insert element 38, of surface microwave waveguide 12 of surface microwave device 10, of the present invention, preferably has a relative permittivity ($\epsilon$) on the order of several units, for example, in the range of between about 1 and about 4.

Figure 4:
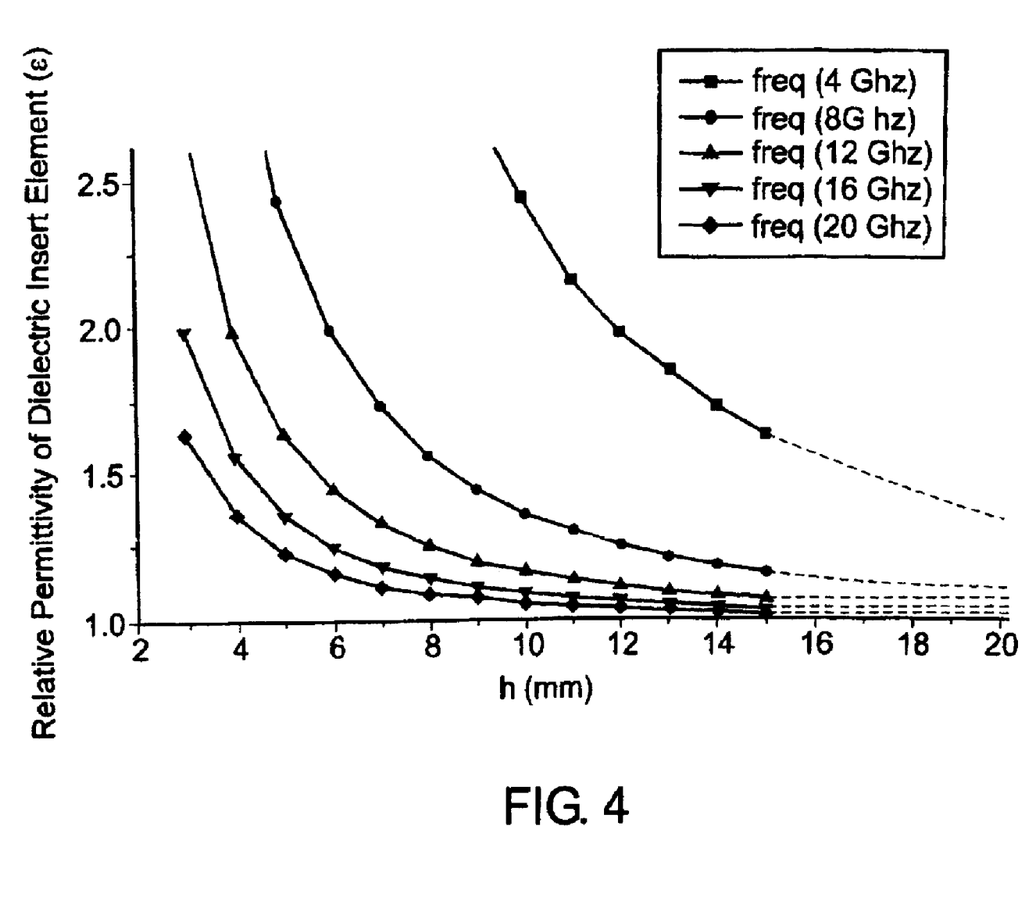
FIG. 4 is a graphical diagram illustrating the functional relationship between the relative permittivity (dielectric constant), $\epsilon$, of the dielectric rectangular insert element and the free space propagation height, h (mm), in the proximate free space region spanning immediately above the externally exposed flat top surface of the dielectric rectangular insert element of the surface microwave waveguide of the surface microwave device of FIG. 1, at different operating microwave frequencies, in accordance with the present invention.

FIG. 4 is a graphical diagram illustrating the functional relationship between the relative permittivity (dielectric constant), $\epsilon$, of dielectric rectangular insert element 38, and the previously described free space propagation, travel, or deflection, height, h (mm), in proximate free space region 16 and immediately above externally exposed flat top surface 48 of dielectric rectangular insert element 38, of surface microwave waveguide 12, of surface microwave device 10 of FIG. 1, at different operating microwave frequencies.

It is apparent from the graph illustrated in FIG. 4, that for dielectric rectangular insert element 38 made of Teflon, a well known low loss dielectric material, having relative permittivity ($\epsilon$) of about 2.5, if measurements are made at an operating frequency of about 20 GHz, optimum sensitivity is obtained for a sheet, board, or web, configured material, about 2 mm thick, whereas a sheet, board, or web, configured material, about 2 cm thick is optimally measured at an operating frequency of about 2 GHz. Changing the relative permittivity ($\epsilon$) of dielectric rectangular insert element 38 within narrow limits makes it possible to significantly change the propagation, travel, or deflection, height, h (mm), within working or active proximate free space region 16 immediately above externally exposed flat top surface 48 of dielectric rectangular insert element 38, and hence the effective operating range of surface microwave waveguide 12, in particular, and of surface microwave device 10, in general.

Referring again to FIGS. 1 and 2, electrically conducting rectangular block 26 is preferably made of a good conducting material, for example, brass, or another similar type of good conducting material. The width of rectangular block 26 preferably does not exceed the wavelength within dielectric rectangular insert element 38. Otherwise, such a configuration would give rise to higher mode microwaves within surface microwave waveguide 12. The depth of rectangular block 26 may vary quite considerably. Changing the ratio between the depth of rectangular block 26 and the thickness of dielectric rectangular insert element 38 serves to vary the portion of electromagnetic energy propagated within proximate free space region 16 immediately above externally exposed flat top surface 48 of dielectric rectangular insert element 38, and thus offers a means of controlling the sensitivity and the resolving power of surface microwave device 10. Moreover, increasing the gap between dielectric rectangular insert element 38, and bottom wall 34 of block 26 helps in case of need in decreasing direct losses during operation of surface microwave waveguide 12.

Accordingly, in Step (b), there is transmitting microwaves into first end 20 of surface microwave waveguide 12, by microwave transmitter adapter assembly 18, such that a first portion of the transmitted microwaves propagate within and through surface microwave waveguide 12 and a second portion of the transmitted microwaves propagate within and through proximate free space region 16 including the material 5, such that parameters (amplitude, phase, attenuation, and phase shift) of the propagating microwaves are perturbed by the material 5 and are a function of density and/or moisture content of the material 5 within proximate free space region 16.

In Step (c), there is receiving the first portion and the second portion of the propagating microwaves exiting second end of the surface microwave waveguide, for forming received microwaves, the parameters (amplitude, phase, attenuation, and phase shift) of the transmitted microwaves and of the received microwaves are useable for determining the density and/or moisture content of the material.

Referring again to FIG. 1, microwave receiver adapter assembly 22, operable for receiving the first portion and the second portion of the propagating microwaves exiting second end 24 of surface microwave waveguide 12, for forming received microwaves, includes: (1) a coaxial waveguide coupling 64, (2) a graded waveguide transition section 66, (3) a microwave output coupling pin 68, (4) a coaxial connector 70, (5) a dielectric plate 72, and (6) a dielectric matching wedge 74.

Accordingly, in Step (c), there is receiving the first portion and the second portion of the propagating microwaves exiting second end 24 of surface microwave waveguide 12, by microwave receiver adapter assembly 22, for forming received microwaves. The parameters (amplitude, phase, attenuation, and phase shift) of the transmitted microwaves and of the received microwaves are useable for determining the density and/or moisture content of the material 5.

Second in importance in surface microwave device 10 assembly are microwave transmitter adapter assembly 18 and microwave receiver adapter assembly 22, which lead microwave energy into and out of surface microwave waveguide 12.

Coaxial waveguide couplings 52 which leads energy in from a microwave transmitter unit, for example, a microwave oscillator, through coaxial connector 58 and microwave input coupling pin 56. Graded waveguide transition section 54 enables the transformation of the TEM wave carried by the cable into an H10 wave within surface microwave waveguide 12. By judicious choice of the dimensions and position of microwave input coupling pin 56, it is possible to obtain good matching between the coaxial cable and surface microwave waveguide 12 over a wide frequency range, as described in "Microwave Engineering And Devices", Lebedev, I. V., Visshaya Shkola, Moscow, 1970, p. 226–294. Graded waveguide transition section 54 makes the H10 wave within surface microwave waveguide match the surface microwave waveguide.

Figure 5:
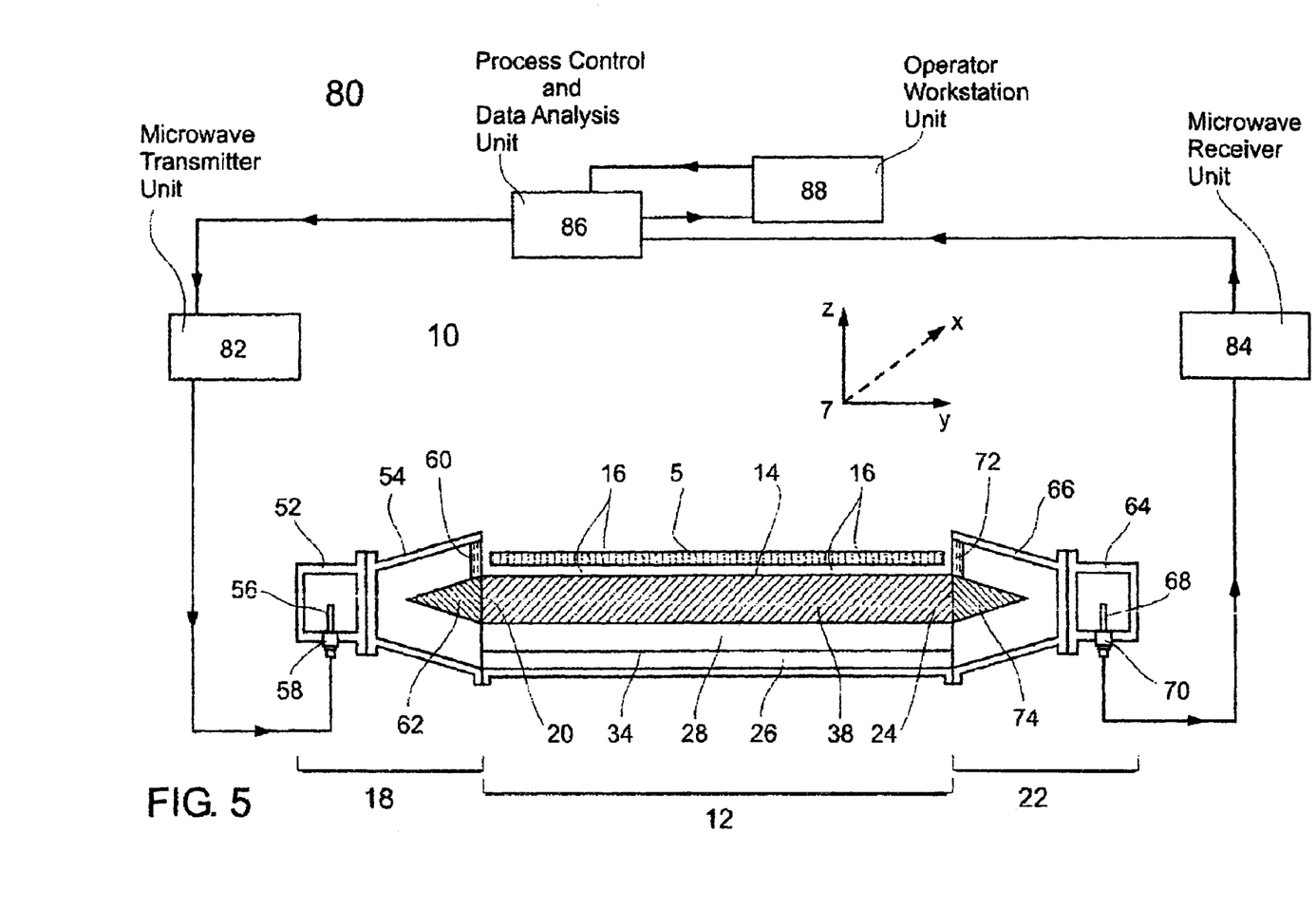
FIG. 5 is a schematic block diagram illustrating an exemplary preferred embodiment of the system, including the surface microwave device of FIG. 1, showing a material being tested, in accordance with the present invention.

FIG. 5 is a schematic block diagram illustrating an exemplary preferred embodiment of the surface microwave system of the present invention, including the surface microwave device of the present invention, showing a material being tested. In FIG. 5, the surface microwave system, herein, referred to as surface microwave system 80, of the present invention, features the following primary components: (a) the previously illustratively described surface microwave device 10 (as shown in FIG. 1) of the present invention; (b) a microwave transmitter unit 82, for example, a microwave oscillator, operatively connected to microwave transmitter adapter assembly 18 of surface microwave device 10, for generating and transmitting microwave radiation to microwave transmitter adapter assembly 18; (c) a microwave receiver unit 84, operatively connected to microwave receiver adapter assembly 22 of surface microwave device 10, for receiving the received microwaves from microwave receiver adapter assembly 22; and (d) a process control and data analysis unit 86, operatively connected to microwave transmitter unit 82 and to microwave receiver unit 84, for controlling the generating and transmitting of the microwave radiation by microwave transmitter unit 82 and of the receiving of the received microwaves by microwave receiver unit 84, and, for processing and analyzing data and information generated during overall operation of surface microwave device 10.

Optionally, surface microwave system 80 further includes: (e) an operator workstation unit 88, operatively connected to process control and data analysis unit 86, for an operator to provide operating commands and instructions for operating surface microwave device 10, and to receive data and information generated during operation of surface microwave device 10.

Optionally, operator workstation unit 88 in surface microwave system 80 includes a display device (not shown) for an operator to display the operating commands and instructions and to display the received data and information generated during operation of surface microwave device 10, in particular, and during operation of surface microwave system 80, in general.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method using surface microwaves for measuring and determining density or moisture content of a material, comprising the steps of:

(a) positioning the material within a proximate free space region spanning immediately above externally exposed flat top surface of a surface microwave waveguide, said surface microwave waveguide is comprised of:

(i) an electrically conducting rectangular block including a rectangular channel which is open to free space, said channel is defined by two parallel inner side walls of said block and a third inner bottom wall of said block orthogonally joining said side walls, said channel extends along entire length of said block, top surface of said block is flat and externally exposed to free space; and (ii) a dielectric rectangular insert element compactly fitting into and along said channel in between said parallel inner side walls of said block and extending along said entire length of said block, each of first end and second end of said insert element is contiguous with corresponding first end and second end of said block, top surface of said insert element is flat, externally exposed to free space, and contiguous with said flat top surface of said block such that said flat top surface of said insert element and said flat top surface of said block form said externally exposed flat top surface of said surface microwave waveguide;

(b) transmitting microwaves into first end of said surface microwave waveguide, such that a first portion of said transmitted microwaves propagate within and through said surface microwave waveguide and a second portion of said transmitted microwaves propagate within and through said proximate free space region including the material, such that parameters of said propagating microwaves are perturbed by the material and are a function of density or moisture content of the material within said proximate free space region; and (c) receiving said first portion and said second portion of said propagating microwaves exiting second end of said surface microwave waveguide, for forming received microwaves, said parameters of said transmitted microwaves and of said received microwaves are useable for determining the density or moisture content of the material.

2. The method of claim 1, wherein step (a) the material is positioned within said proximate free space region, such that the material does not contact said externally exposed flat top surface of said surface microwave waveguide.

3. The method of claim 1, wherein steps (b) and (c) the material continuously or intermittently moves along its longitudinal axis.

4. The method of claim 1, wherein majority of said transmitted microwaves propagate within said dielectric rectangular insert element.

5. The method of claim 1, wherein step (b) further comprises changing speed of said propagating microwaves, thereby changing propagation distance of electromagnetic field of said propagating microwaves, within and through said proximate free space region.

6. The method of claim 1, wherein said dielectric rectangular insert element has a relative permittivity in a range of between about 1 and about 4.

7. The method of claim 1, wherein said dielectric rectangular insert element is made of Teflon.

8. The method of claim 1, wherein width of said electrically conducting rectangular block does not exceed wavelength of said transmitted microwaves propagating within said dielectric rectangular insert element.

9. The method of claim 1, wherein the material is a dielectric material.

10. The method of claim 1, wherein the material is configured as a thin sheet, board, or web.

11. The method of claim 1, wherein said surface microwave waveguide is operated at an operating frequency of about 20 GHz, or of about 2 GHz.

12. A device using surface microwaves for measuring and determining density or moisture content of a material, comprising:

(a) a surface microwave waveguide having an externally exposed flat top surface immediately above which spans a proximate free space region within which the material is positioned, said surface microwave waveguide is comprised of:

(i) an electrically conducting rectangular block including a rectangular channel which is open to free space, said channel is defined by two parallel inner side walls of said block and a third inner bottom wall of said block orthogonally joining said side walls, said channel extends along entire length of said block, top surface of said block is flat and externally exposed to free space; and (ii) a dielectric rectangular insert element compactly fitting into and along said channel in between said parallel inner side walls of said block and extending along said entire length of said block, each of first end and second end of said insert element is contiguous with corresponding first end and second end of said block, top surface of said insert element is flat, externally exposed to free space, and contiguous with said flat top surface of said block such that said flat top surface of said insert element and said flat top surface of said block form said externally exposed flat top surface of said surface microwave waveguide;

(b) a microwave transmitter adapter assembly for transmitting microwaves into first end of said surface microwave waveguide, such that a first portion of said transmitted microwaves propagate within and through said surface microwave waveguide and a second portion of said transmitted microwaves propagate within and through said proximate free space region including the material, such that parameters of said propagating microwaves are perturbed by the material and are a function of density or moisture content of the material within said proximate free space region; and (c) a microwave receiver adapter assembly for receiving said first portion and said second portion of said propagating microwaves exiting second end of said surface microwave waveguide, for forming received microwaves, said parameters of said transmitted microwaves and of said received microwaves are useable for determining the density or moisture content of the material.

13. The device of claim 12, wherein the material is positioned within said proximate free space region, such that the material does not contact said externally exposed flat top surface of said surface microwave waveguide.

14. The device of claim 12, wherein the material continuously or intermittently moves along its longitudinal axis.

15. The device of claim 12, wherein majority of said transmitted microwaves propagate within said dielectric rectangular insert element.

16. The device of claim 12, wherein changing speed of said propagating microwaves changes propagation distance of electromagnetic field of said propagating microwaves, within and through said proximate free space region.

17. The device of claim 12, wherein said dielectric rectangular insert element has a relative permittivity in a range of between about 1 and about 4.

18. The device of claim 12, wherein said dielectric rectangular insert element is made of Teflon.

19. The device of claim 12, wherein width of said electrically conducting rectangular block does not exceed wavelength of said transmitted microwaves propagating within said dielectric rectangular insert element.

20. The device of claim 12, wherein the material is a dielectric material.

21. The device of claim 12, wherein the material is configured as a thin sheet, board, or web.

22. The device of claim 12, wherein said surface microwave waveguide is operated at an operating frequency of about 20 GHz, or of about 2 GHz.

23. A system using surface microwaves for measuring and determining density or moisture content of a material, comprising:
  (a) a surface microwave device, comprising:
    (i) a surface microwave waveguide having an externally exposed flat top surface immediately above which spans a proximate free space region within which the material is positioned, said surface microwave waveguide is comprised of:
      (1) an electrically conducting rectangular block including an open rectangular channel whose top is open to free space, said channel is defined by two parallel inner side walls of said block and a third inner bottom wall of said block orthogonally joining said side walls, said channel extends along entire length of said block, top surface of said block is flat and externally exposed to free space; and
      (2) a dielectric rectangular insert element compactly fitting into and along said channel in between said parallel inner side walls of said block and extending along said entire length of said block, each of first end and second end of said insert element is contiguous with corresponding first end and second end of said block, top surface of said insert element is flat, externally exposed to free space, and contiguous with said flat top surface of said block such that said flat top surface of said insert element and said flat top surface of said block form said externally exposed flat top surface of said surface microwave waveguide;
    (ii) a microwave transmitter adapter assembly for transmitting microwaves into first end of said surface microwave waveguide, such that a first portion of said transmitted microwaves propagate within and through said surface microwave waveguide and a second portion of said transmitted microwaves propagate within and through said proximate free space region including the material, such that parameters of said propagating microwaves are perturbed by the material and are a function of density or moisture content of the material within said proximate free space region; and
    (iii) a microwave receiver adapter assembly for receiving said first portion and said second portion of said propagating microwaves exiting second end of said surface microwave waveguide, for forming received microwaves, said parameters of said transmitted microwaves and of said received microwaves are useable for determining the density or moisture content of the material;
  (b) a microwave transmitter unit, operatively connected to said microwave transmitter adapter assembly of said surface microwave device, for generating and transmitting microwave radiation to said microwave transmitter adapter assembly;
  (c) a microwave receiver unit, operatively connected to said microwave receiver adapter assembly of said surface microwave device, for receiving said received microwaves from said microwave receiver adapter assembly; and
  (d) a process control and data analysis unit, operatively connected to said microwave transmitter unit and to said microwave receiver unit, for controlling said generating and transmitting said microwave radiation by said microwave transmitter unit and of said receiving said received microwaves by said microwave receiver unit, and, for processing and analyzing data and information generated during operation of said surface microwave device.

24. The system of claim 23, further including an operator workstation unit, operatively connected to said process control and data analysis unit, for an operator to provide operating commands and instructions for operating said surface microwave device, and to receive data and information generated during operation of said surface microwave device.

25. The system of claim 24, wherein said operator workstation unit includes a display device for an operator to display said operating commands and instructions and to display said received data and information generated during operation of said surface microwave device.

26. The system of claim 23, wherein the material is positioned within said proximate free space region, such that the material does not contact said externally exposed flat top surface of said surface microwave waveguide.

27. The system of claim 23, wherein the material continuously or intermittently moves along its longitudinal axis.

28. The system of claim 23, wherein majority of said transmitted microwaves propagate within said dielectric rectangular insert element.

29. The system of claim 23, wherein changing speed of said propagating microwaves changes propagation distance of electromagnetic field of said propagating microwaves, within and through said proximate free space region.

30. The system of claim 23, wherein said dielectric rectangular insert element has a relative permittivity in a range of between about 1 and about 4.

31. The system of claim 23, wherein said dielectric rectangular insert element is made of Teflon.

32. The system of claim 23, wherein width of said electrically conducting rectangular block does not exceed wavelength of said transmitted microwaves propagating within said dielectric rectangular insert element.

33. The system of claim 23, wherein the material is a dielectric material.

34. The system of claim 23, wherein the material is configured as a thin sheet, board, or web.

35. The system of claim 23, wherein said surface microwave waveguide is operated at an operating frequency of about 20 GHz, or of about 2 GHz.

* * * * *